United States Patent [19]
Macandrew et al.

[11] Patent Number: 5,785,053
[45] Date of Patent: Jul. 28, 1998

[54] INSERTER FOR THE POSITIONING OF AN INTRAUTERINE DEVICE

[75] Inventors: John Macandrew, St. Neots; John Conway, Sawston; Michael Paton; Richard Gardner, both of Royston, all of Great Britain; Ilkka Rauramo, Espoo; Matti Lehtinen, Piispanristi, both of Finland

[73] Assignee: Leiras Oy, Turku, Finland

[21] Appl. No.: 849,550

[22] PCT Filed: Dec. 5, 1995

[86] PCT No.: PCT/FI95/00666

§ 371 Date: Jun. 2, 1997

§ 102(e) Date: Jun. 2, 1997

[87] PCT Pub. No.: WO96/18365

PCT Pub. Date: Jun. 20, 1996

[30] Foreign Application Priority Data

Dec. 15, 1994 [FI] Finland .................... 945895

[51] Int. Cl.⁶ .................... A61F 06/06; A61B 17/42
[52] U.S. Cl. .................... 128/840; 606/119
[58] Field of Search .................... 128/830–841; 606/119, 108

[56] References Cited

U.S. PATENT DOCUMENTS

| | | |
|---|---|---|
| 3,678,947 | 7/1972 | Soichet . |
| 3,750,661 | 8/1973 | Knoch . |
| 4,026,281 | 5/1977 | Mayberry et al. .................... 128/840 |
| 4,143,656 | 3/1979 | Holmes . |
| 4,353,363 | 10/1982 | Quesada . |
| 4,721,105 | 1/1988 | Wildemeersch .................... 128/840 |

FOREIGN PATENT DOCUMENTS

| | | |
|---|---|---|
| 0049660 | 4/1982 | European Pat. Off. . |
| 53268 | 4/1978 | Finland . |
| 67999 | 7/1985 | Finland . |
| WO93/15699 | 8/1993 | WIPO .................... 128/840 |
| WO 94/27531 | 12/1994 | WIPO . |

*Primary Examiner*—Glenn K. Dawson
*Attorney, Agent, or Firm*—Adduci, Mastriani & Schaumberg, L.L.P.

[57] ABSTRACT

An inserter for the positioning of an intrauterine device in the uterus, which inserter includes a plunger, a handle attached to the plunger, a string for the removal of the IUD, a locking device to lock the string in such a way that the IUD remains immobile in relation to the plunger, and a protective tube around the plunger. The protective tube is arranged in relation to the plunger in such a way that it can be pushed, at the forward end that goes into the uterus, past the plunger at distance (L), which corresponds substantially to the length of the IUD assembled for insertion. The stop members ensure that the front edge of the protective tube is stopped in a configuration in which the hemispherical tips of the wings of the transverse member of a T-shaped IUD remain partly uncovered by the protective tube, but the wings nevertheless remain pressed against each other.

9 Claims, 4 Drawing Sheets

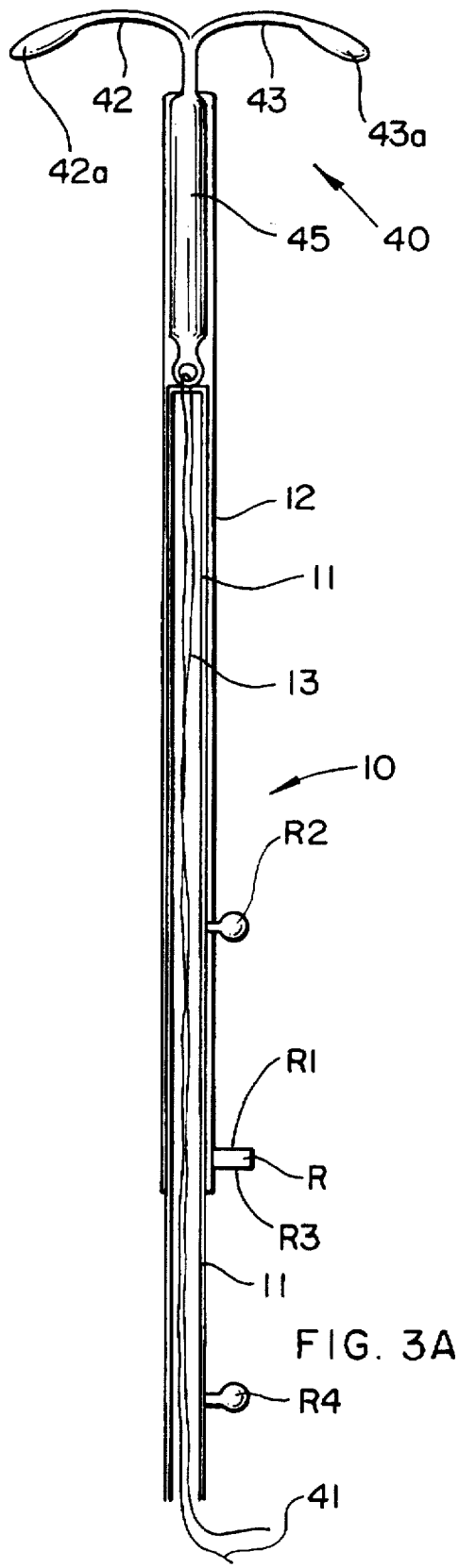
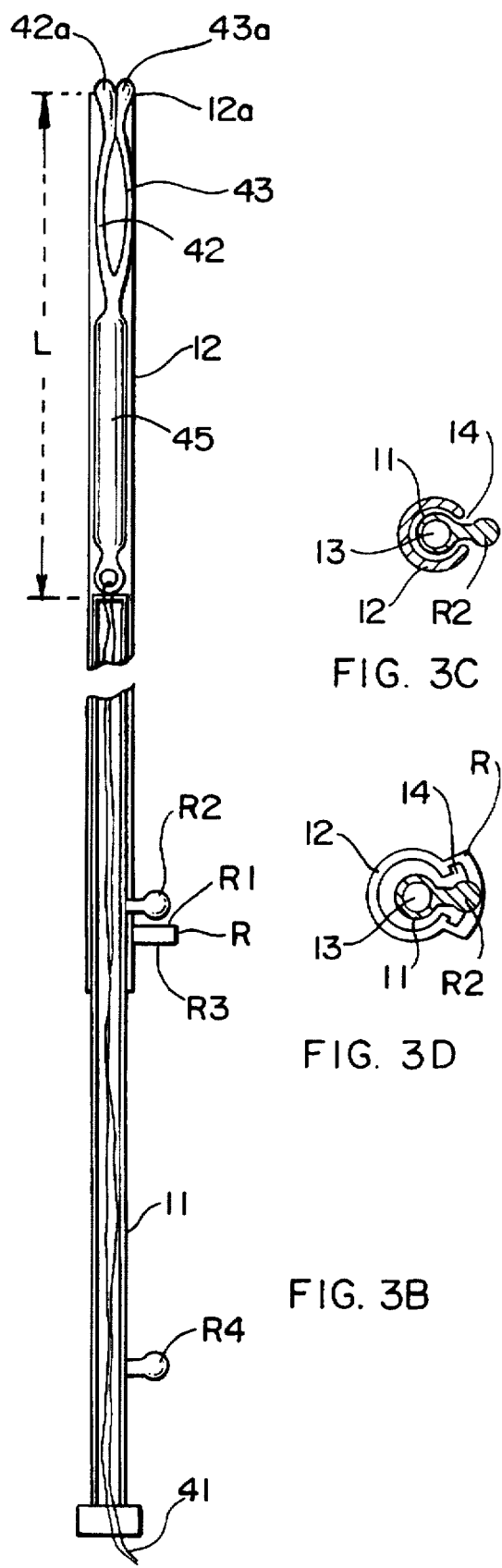
FIG. 3A FIG. 3B FIG. 3C FIG. 3D

INSERTER FOR THE POSITIONING OF AN INTRAUTERINE DEVICE

BACKGROUND OF THE INVENTION

The invention relates to an inserter for the positioning of an intrauterine device. The invention also relates to an assembly of the inserter and the intrauterine device.

An intrauterine contraceptive device (also called an intrauterine device or IUD) in common use is a T-shaped object fabricated of plastic material, which object consists of an elongate member having at one end a transverse member comprising two wings, the elongate member and the transverse member forming a substantially T-shaped piece when the device is positioned in the uterus. The elongate member has a copper wire wound partly around it, said wire being capable of releasing copper ions. The device has an attached thread long enough to protrude out of the cervical canal when the device is in position in the uterus. The device is introduced into the uterus by means of a separate inserter, the device being in a contracted state during insertion in order to facilitate the introduction of the device through the cervical canal. The tips of the wings of the transverse member are hemispherical in order to facilitate the introduction of the device, contained within the inserter, through the cervical canal.

In addition to T-shaped IUD's also devices shaped like a ring, a "7" or an "S", for example, are known.

Also IUD's capable of releasing hormones or other active agents exist, and they are used either for contraception or for the treatment of hormonal troubles.

Several types of inserters exist for the positioning of intrauterine devices. The most common inserter for T-shaped IUD's consists of a plunger with a handle, inside a protective tube. Preparative to the positioning the device in the uterus, the IUD, which is located at the end of the plunger, is retracted towards the handle so that the device enters the tube, and the wings of the transverse member of the device bend towards each other. Then the protecting tube with its contained IUD are introduced through the cervical canal. When the device is correctly positioned it is released by retracting the protecting tube towards the outside. The wings of the transverse member then expand, and the device assumes the shape of a "T".

A contraceptive device, which is available on the market and which releases levonorgestrel, consists of a T-shaped IUD having an elongate member fabricated of polyethylene equipped with a reservoir adjusted around it and containing the hormone levonorgestrel. The device is sold in sterile packaging together with the inserter with the plunger, which is a solid piece, contained within the protecting tube. The T-shaped device is positioned at the forward end of the plunger with the hormone-containing elongate member protected by the tube. The wings of the transverse member, on the other hand, are expanded in order to prevent fatigue. The strings by which the T-shaped device is retracted towards the outside run between the plunger and the protective tube and end at the end of the handle. FIG. 1 illustrates one such device. The T-shaped IUD's having an elongate member wound with copper wire are packaged in a similar manner.

A problem associated with the inserters of T-shaped devices containing active compounds regards the attainment of the correct positioning of the IUD within the protective tube. The difficulty is due to the greater diameter of the elongate member of these devices as compared to the copper wire-containing IUD, which means that the diameter of the protective tube also is greater. The hemispherical end pieces of the wings of the transverse member are small in relation to the diameter of the protective tube. It is therefore extremely important that these end pieces are in the exactly correct position in relation to the edge of the protective tube at the moment of introducing the device in the uterus. FIG. 2A shows an example of the correct positioning of the T-shaped device in the protective tube of the inserter. If the IUD is pulled into the protective tube by means of the removal string, which is the case with the devices described above, it is understandable that it is difficult to make the IUD stop in the correct position if the relative movement of the protective tube and the plunger is not restricted by any stop member. Pulling with too much force easily makes the tips of the wings of the transverse member enter almost completely into the protective tube (FIG. 2B). During the insertion of the device, the sharp edges of the protective tube may interfere with the introduction of the device through the cervical canal. If, on the other hand, the device is not drawn deep enough into the protective tube, a situation occurs like that shown in FIG. 2C, in which the wings of the transverse member project outwardly because of a too wide protective tube. The diameter at the level of the wings remains too wide, which makes the introduction of the device during insertion more difficult. It is easier to make the wings stop in the correct position (FIG. 2D) in the case of the copper-wire devices, because the tube is narrow in relation to the wings. Therefore there is no risk of the wings being drawn too deep into the tube even by forceful pulling.

Methods are known in the patent literature, according to which the IUD is placed within a protective tube when the device is being introduced into the uterus. GP Patent 1,600, 717 describes an inserter suitable for T-shaped or Y-shaped IUD's. The IUD is retracted into the protective tube by means of an attached string. Patent publications U.S. Pat. No. 3,842,826 and WO 94/13,233 also describe methods for retracting the IUD into a protective tube before the insertion of the IUD. GB 1,403,393 describes a method in which an IUD contained in a protective tube is pushed towards the end of the tube before the insertion of the device.

No method has been described earlier in which an IUD is introduced into the protective tube by pushing the tube over the device, or by pulling the device into the protective tube, where the relative movement of the plunger and protective tube is restricted by a stop member to ascertain that the correct configuration of the IUD is achieved.

BRIEF SUMMARY OF THE INVENTION

It is the objective of the present invention to introduce a means to overcome the problems described above and to produce a new kind of inserter which allows the correct positioning of an IUD also in those cases in which the elongate member of a T-shaped IUD contains active material, which involves a diameter larger than that of the elongate member of a copper-wire IUD. It is also our objective to produce an inserter which is firm and stable and where no risk of non-resilient bending of the protective tube is involved.

BRIEF DESCRIPTION OF THE DRAWINGS

The invention will now be described by referral to the following drawings, wherein FIGS. 3A–3D illustrate the operating principle of an inserter according to the invention

DETAILED DESCRIPTION OF A PREFERRED EMBODIMENT

Figures 1A, 1B:
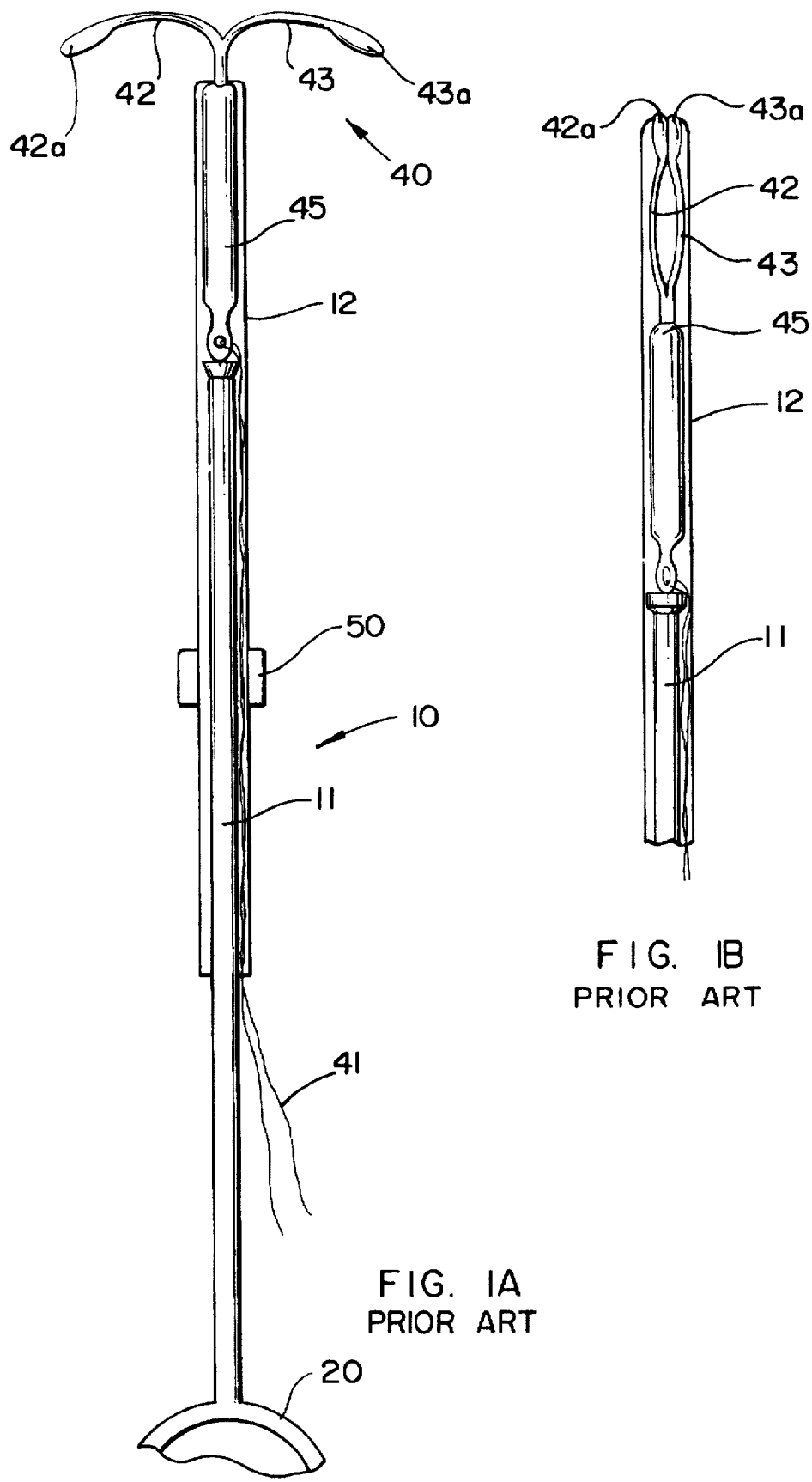
FIGS. 1A–1B illustrate as the technical level the unitary combination of an inserter and an IUD
Figure 2A:
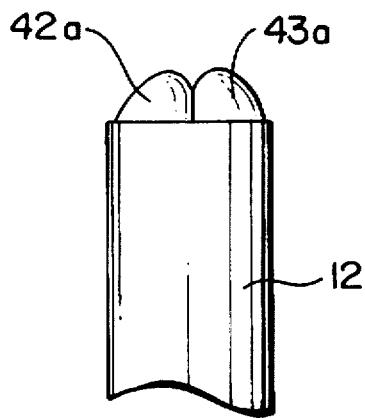
FIGS. 2A–2D illustrate T-shaped IUD's retracted into the protective tube in the correct or the wrong manner
Figure 2B:
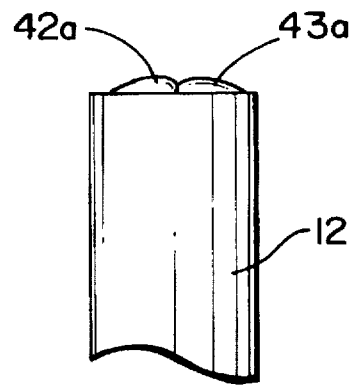
Figure 2C:
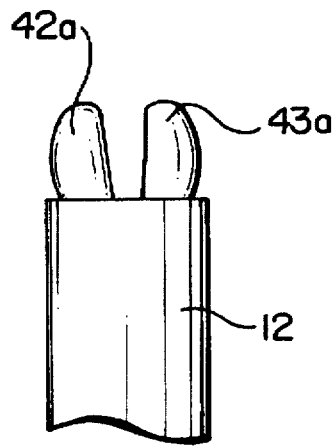
Figure 2D:
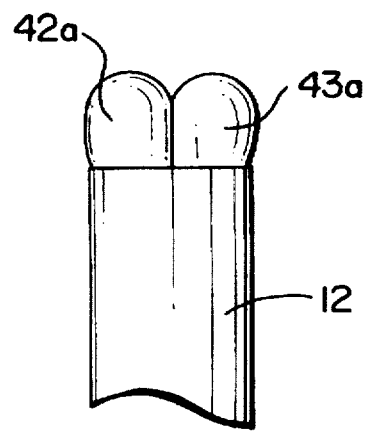

FIG. 1A shows a design according to the technical level, in which the T-shaped elongate member 45 of the IUD 40 has been placed in the protective tube 12 of the inserter, and the wings 42 and 43 of the transverse member of the IUD are expanded. The plunger 11 is a solid rod with a handle 20 at one end. The withdrawal string(s) 41 run(s) in the space between plunger 11 and protective tube 12. Reference No. 50 refers to a signalling device which can be slid along the surface of the protective tube and placed in a desired location. When the IUD is inserted the signalling device is in contact with the cervical canal and signals the correct depth of positioning the IUD. Before the device is made operational the withdrawal string is pulled in the direction of the handle 20. This allows the entrance of the IUD into the protective tube 12, at which moment the wings 42 and 43 are folded against each other. FIG. 1B shows the IUD, protected by the tube 12, in the form in which it is inserted. After the assembly of FIG. 1B has been positioned in the uterus so that the IUD is correctly located the IUD is released by retracting the protective tube 12 outwardly while retaining the plunger 11 stationary.

FIGS. 3A and 3B show an embodiment of the invention, which illustrates the operating principle. FIG. 3A shows an inserter 10 with an IUD 40 placed in the front end (entry into the uterus) so that the elongate member 45 is inside the protective tube 12. Before insertion the string 41 is tightened and locked in the locking device (15) associated with the plunger 11, with the tip of the elongate member abutting the end of the plunger. The method described in this figure involves a hollow plunger, and the string 41 runs advantageously in the bore 13 of the plunger. The string thus slides freely, and there is no risk of its getting jammed between the plunger and the tube. The plunger has two attached radial projecting stop members R2 and R4. The jacket of the protective tube 12 has an axially directed slot 14 corresponding to the stop members R2 and R4 (the transverse cross-section is shown in FIG. 3C) and designed to allow the movement of the protective tube 12 in axial direction. The jacket of the protective tube has an attached stop member R with stopping surfaces R1 and R3 projecting in the direction of the radius of the plunger. FIG. 3D is a cross-section showing stop member R. Preparative to use of the device the tightening and locking of the withdrawal string is checked. Then, while holding the handle of the plunger, the protective tube is pushed towards the IUD until surface R1 of stop member R abuts stop member R2, thereby stopping the movement of the protective tube. At this moment the IUD is substantially inside the protective tube, and ready for insertion (FIG. 3B). The location of the stop members R1 and R2 has been designed such as to allow pushing the protective tube past the plunger at a desired distance L, which substantially corresponds to the length of the IUD assembled for insertion. The stop members R1 and R2 are advantageously located so that the edge 12a of the protective tube that goes into the uterus is stopped at a level at which the hemispherical tips 42a, 43a of the wings 42, 43 of the transverse member of a T-shaped IUD partly remain uncovered by the protective tube 12, while the wings 42, 43 still remain together.

Alternatively, the surface R1 of the stop member R can be kept in contact with stop member R2, wherein the protective tube extends past the plunger at a distance that essentially corresponds to the length of the IUD assembled for insertion into the uterus. If the IUD is positioned in the device so that the elongate member 45 is positioned inside the protective tube but the wings 42, 43 are outside the protective tube, the IUD can be positioned in the correct position for inserting by pulling the IUD into the protective tube.

The device according to FIG. 3B is pushed into the uterus until the IUD is in the correct location. The IUD is released from the protective tube, while retaining the plunger absolutely stationary, by retracting the protective tube towards the handle until the stop surface R3 abuts the stop member R4 attached to the plunger. The location of the stop devices R3 and R4 has been selected so that, when these stop devices meet, they indicate clearly the moment at which the IUD, at the forward end of the plunger, has been released from the protective tube as it moves towards the handle. The stop member R4 may but does not need to be constructed such as to stop the movement of the protective tube in the direction of the handle.

The stop members R2 and R4 need not, as shown in FIGS. 3A–3D, be attached to the plunger itself. Instead, they may form part of a member which is itself connected to the plunger. The same applies to the stop members R1 and R3: They may be attached to the protective tube itself or to a member connected to the protective tube. The stop members R1 and R3 may form part of the same member R, like in FIGS. 3A–3B, but they may also be separate members.

The plunger is advantageously hollow or has a groove running in the axial direction and allowing the string 41 to slide freely in it.

Figure 4A:
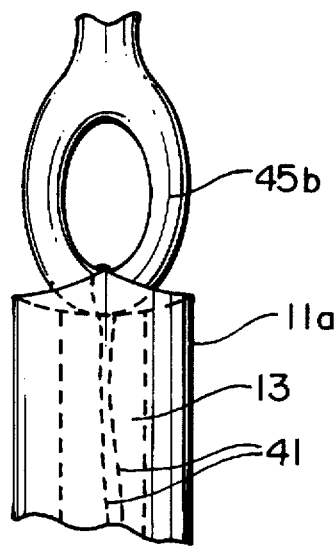
FIGS. 4A–4B illustrate the shape of the end of the plunger
Figure 4B:
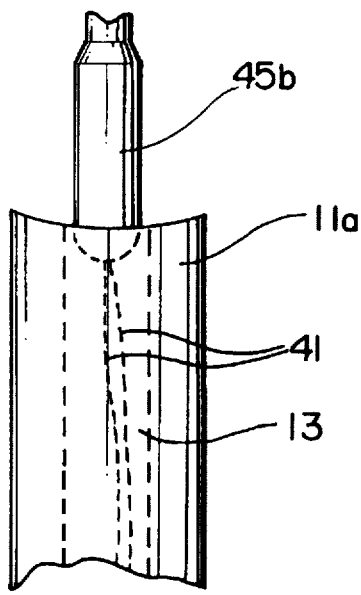

It is important in the insertion of a T-shaped IUD that the wings can be projected laterally and not forward or backward (as considered from the patient). The directional stiffness of an IUD during insertion can be ensured, for instance, by shaping the forward end of the plunger such that the IUD assumes a specified constant configuration when the string is retracted. The IUD thus will not be twisted during insertion. An example of such a design is presented in FIGS. 4A and 4B. The end 45b of the elongate member abutting the plunger is shaped like an eyelet, which has an attached string 41 for retracting. The figures show that the forward end 11a of the plunger is not level but hollowed out to form a sort of shallow funnel. When the string 41 attached to the eyelet 45b is retracted the eyelet 45b slides into the funnel and is caught there. FIG. 4A is a front view and FIG. 4B a side view of the eyelet 45.

The forward parts (directed towards the uterus) of the plunger and the protective tube can be straight or curved so as to conform to the anatomy of the uterus.

Figure 5:
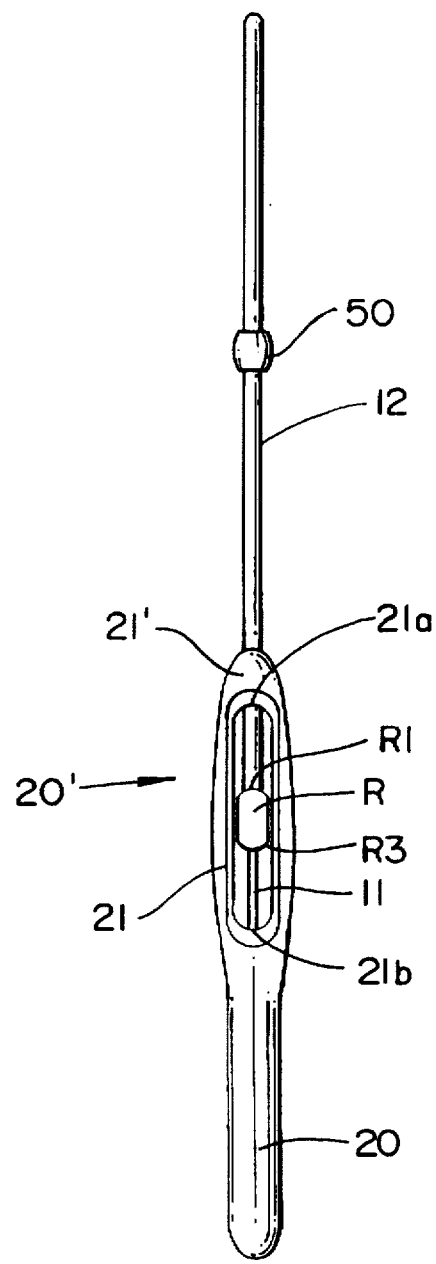
FIG. 5 illustrates an embodiment of the invention

A suitable embodiment of the invention is illustrated in FIG. 5. The forward part 20' of the handle 20 forms a construction 21 running in the longitudinal direction of the plunger. The construction has in the forward end 21' a channel in which the protective tube 12 will slide in the longitudinal direction. The protective tube has a knob R at the distal end (away from the uterus). The surface R1, in the direction of the uterus, of the knob R and the surface 21a, in the direction of the handle 20, of the end 21' of the construction 21, together form a pair of stop members R1, R2. The edge R3, in the direction away from the uterus, of knob R and the surface 21b of the base of the construction 21 together form a pair of stop members R3, R4.

If desired one or more signalling devices may be arranged between the stop members R1/R2 and R3/R4. Such a signalling device can, for instance, be located in such a way that the doctor, when he prepares to release the IUD, will notice the moment at which the wings of the transverse member of the IUD have been released from the protective tube while the elongate member is still protected by the tube. Such a signalling device must not, of course, effectively stop the retraction of the tube, because then the IUD could not be released.

This invention provides for an inserter that allows the easy positioning of an IUD in a predetermined location in the protective tube, because the stop members guarantee an accurate positioning of the IUD during insertion and its accurate release. According to this invention it is not necessary to provide so much clearing between the plunger and the protective tube as in inserters in which the IUD's are positioned by retraction without any stop member which stops the movement of the IUD. This results in an extremely stable construction, which involves no risk of irremediable bending of the tube.

The inserter according to the invention is particularly suitable for the positioning of T-shaped IUD's, but it is also applicable to other types of IUD as long as these can be managed to enter the protective tube by appropriate arrangements.

While the invention is applicable to the positioning of IUD's of the copper-wire type the advantages will be better appreciated in the case of devices containing active agents. An inserter according to this invention is particularly suitable for the positioning of such a T-shaped IUD which has an elongate member 45 having a jacket-like polymeric reservoir containing an active agent wound around it.

Suitable active agents include hormones used for the treatment of menopausal troubles or for contraception.

Those versed in the art will appreciate that many different variations and adaptations of the present invention fall within the scope of the claims presented in the following section.

We claim:

1. An inserter for the positioning of an essentially T-shaped intrauterine device (IUD), said IUD comprising an elongated body having a transverse member attached at one end of said body, said transverse member comprising two wings, which inserter comprises a plunger having a front end adapted to receive the IUD and a rear end, a handle formed from or attached to the rear end of the plunger, a locking device operatively attached to said plunger, said locking device adapted to lock a string attached to the IUD in such a way that the IUD remains immobile in relation to the front end of the plunger, and a protective tube adapted to contain said IUD in a contracted configuration in which said wings of the transverse member of an essentially T-shaped IUD are pressed against each other, said protective tube having a forward end adapted for insertion into the uterus and a rear end, wherein the protective tube is fitted in slidable relationship around the plunger in such a way that it can be pushed, at the forward end, past the plunger at a distance which corresponds substantially to the length of the IUD in said contracted configuration, and wherein the rear end of the protective tube, has a first stop surface operatively attached thereto, and wherein the plunger, has a second stop surface operatively attached thereto located in such a way that the said second stop surface will contact said first stop surface and thereby stop movement of the protective tube in the direction of the uterus when the forward end of the protective tube is in a position in which the tips of said wings of the transverse member of said T-shaped IUD remain partly uncovered by the protective tube, but the wings nevertheless remain pressed against each other.

2. The inserter according to claim 1, wherein the rear end of the protective tube, has a third stop surface operatively attached thereto, and wherein the plunger has a fourth stop surface operatively attached thereto, such that the said third and fourth stop surfaces, when they abut, indicate the moment at which the protective tube, when moving towards the handle, releases the IUD associated with the forward end of the plunger.

3. The inserter according to claim 2, wherein said handle includes a hollow front end which encompasses a portion of said plunger and said protective tube, said handle having a longitudinal open channel coaxial with said protective tube, wherein said first and third stop surfaces are located on opposite sides of a knob attached to or formed on said protective tube, with said knob positioned in said channel; and wherein said second and fourth stop surfaces comprise the opposite surfaces of the handle forming channel.

4. The inserter according to claim 1, wherein the plunger has a hollow bore so that a withdrawal string of said IUD can run in the bore of the plunger.

5. The inserter according to claim 1 wherein the plunger has a concave front end in which a tip of the elongated body of the IUD is caught when the string is tightened, and twisting of the IUD during insertion is thus prevented.

6. The inserter according to claim 1 wherein parts of the plunger and the protective tube that are adapted to be directed towards the uterus are curved.

7. The inserter according to claim 1, in combination with an intrauterine device (IUD).

8. The combination according to claim 7, wherein an elongate member of the IUD comprises a core part around which a jacket-like polymeric reservoir containing an active agent has been fitted.

9. The combination according to claim 8, wherein the active agent is a hormone used for the treatment of menopausal troubles or for contraception.

* * * * *